United States Patent [19]

Knoll et al.

[11] Patent Number: 4,778,811
[45] Date of Patent: Oct. 18, 1988

[54] PHARMACEUTICAL COMPOSITIONS OF 2-METHYL-THIAZOLO[4,5-C]QUINOLINE

[75] Inventors: József Knoll; Lujza Petöcz; Attila Mándi; Edit Berényi née Poldermann; Katalin Budai née Simonyi; Berta Knoll; Zsuzsa Fürts; Julia Timár; Gabriella Zsila; Ildikó Niklya, all of Budapest, Hungary

[73] Assignee: EGIS Gyogyszergyar, Budapest, Hungary

[21] Appl. No.: 929,341

[22] Filed: Nov. 12, 1986

[30] Foreign Application Priority Data

Nov. 12, 1985 [HU] Hungary ................ 4302/85

[51] Int. Cl.$^4$ ............... A61K 31/47; C07D 513/04
[52] U.S. Cl. ........................... 514/293; 546/83
[58] Field of Search ............ 546/80, 83; 514/292, 514/3

[56] References Cited

U.S. PATENT DOCUMENTS 4,666,916  5/1987  Schneider ................ 546/80

OTHER PUBLICATIONS

Chemical Abstracts, vol. 60, Abst. No. 694d, 1964.
*JACS*, vol. 69, 1947, pp. 365-371.

*Primary Examiner*—Mary C. Lee
*Assistant Examiner*—Zinna Northington
*Attorney, Agent, or Firm*—Keil & Weinkauf

[57] ABSTRACT

It has been found that 2-methyl-thiazolo[4,5-c]quinoline and pharmaceutically acceptable acid addition salts and hydrates thereof possess valuable central nervous depressive properties being different from those of benzodiazepines. The invention relates to pharmaceutical compositions comprising as active ingredient 2-methyl-thiazolo[4,5-c]quinoline of the Formula I

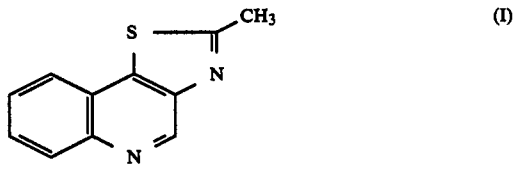

or a pharmaceutically acceptable acid addition salt or hydrate thereof.

5 Claims, No Drawings

PHARMACEUTICAL COMPOSITIONS OF 2-METHYL-THIAZOLO[4,5-C]QUINOLINE

This invention relates to pharmaceutical compositions and a process for the preparation thereof. More particularly it is directed to pharmaceutical compositions having central nervous depressant effect and a process for the preparation of the said compositions.

According to an aspect of the present invention there is provided a pharmaceutical composition comprising a therapeuticaly active amount of 2-methyl-thiazolo[4,5-c]quinoline of the Formula I

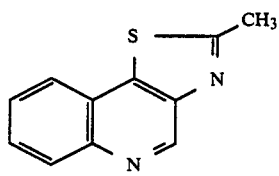

or a pharmaceutically acceptable acid addition salt thereof or a hydrate of the base or an acid addition salt thereof in admixture with suitable inert solid or liquid therapeutical carriers.

According to a further feature of the present invention there is provided a process for the preparation of pharmaceutical compositions which comprises admixing 2-methyl-thiazolo[4,5-c]quinoline of the Formula I, or a pharmaceutically acceptable acid addition salt thereof or a hydrate of the base or an acid addition salt thereof with suitable inert non-toxic solid or liquid pharmaceutical carriers.

According to a still further feature of the present invention there is provided the use of 2-methyl-thiazolo[4,5-c]quinoline of the Formula I or a pharmaceutically acceptable acid addition salt thereof or a hydrate of the base or an acid addition salt thereof for the preparation of pharmaceutical compositions.

2-Methyl-thiazolo[4,5-c]quinoline and the hydrochloride thereof were described by Bachman et al. [J. Am. Chem. Soc. 69, 365–371 (1947)]. The authors prepared the said compound by reacting 3-amino-4-methyl-quinoline with acetic anhydride and converting the 2-methyl-thiazolo[4,5-c]quinoline thus obtained into the hydrochloride salt by treatment with hydrochloric acid. The said publication is, however, completely silent in disclosing any useful biological activity of 2-methyl-thiazolo[4,5-c]quinoline and the hydrochloride thereof. It was merely stated that the said compound proved to be completely ineffective against malaria.

The present invention is based on the recognition that 2-methyl-thiazolo[4,5-c]quinoline of the Formula I and pharmaceutically acceptable acid additions salts thereof possess a valuable and highly interesting and special spectrum of effect. The compound of the Formula I and pharmaceutically acceptable acid addition salts thereof exhibit a central nervous depressant effect being different from that of known central depressive agents. Contrary to major tranquillants, the compound of the Formula I does not inhibit non-specific activation mechanisms and therefore even if administered in high doses it enables the escape of animals in the one session unconditioned reflex test. Conventional tranquillants cause complete inhibition of the said reaction even in minimal doses.

The main difference of action between the compound of the Formula I and benzodiazepines resides in the fact that the compound of the Formula I is void of any spasmolytic effect and simultaneously shows a significantly stronger central depressant effect than benzodiazepines. Moreover, the compound of the Formula I is not bound by benzodiazepine receptors.

The ethane sulfonate of the compound of the Formula I shows particularly preferred pharmacological properties. This compound is new, never described in prior art.

According to a still further feature of the present invention there is provided the new 2-methyl-thiazolo[4,5-c]quinoline-ethanesulfonate.

The pharmacological activity of 2-methyl-thiazolo[4,5-c]quinoline and pharmaceutically acceptable acid addition salts thereof is demonstrated by the following tests:

1. Acute Toxicity

Acute toxicity was assessed on CFY rats (100–160 g). Groups of 10 rats were used. The compounds were administered orally (in volume of 10 ml/kg) and s.c. (in volume of 5 ml/kg). In the case of oral administration the animals starved for 16 h before the experiment. Each dose was administerd to a group of animals equally subdivided into males and females. Deaths occuring within 48 h were considered. $LD_{50}$ values were calculated on the basis of the graphical method of Litchfield and Wilcoxon.

2-Methyl-thiazolo[4,5-c]quinoline-hydrochloride $LD_{50}$ = 160 mg/kg i.v.
900 mg/kg p.o.
750 mg/kg s.c.

2-Methyl-thiazolo[4,5-c]quinoline-ethanesulfonate $LD_{50}$ = 950 mg/kg p.o.
810 mg/kg s.c.

cl 2. Hot Plate Test

The method of Woolfe and McDonald (1944) modified by Porszasz and Herr (1950) was used. The effect of each dose of the drugs was checked on a group of 10 rats. The experiments were performed on metal plates maintained at 56° C. The latency time of pain reactions was determined prior to and 1 h after the administration of the test compound. It was regarded as 100% effect if the reaction time was prolonged by more than 2.5 times the control value.

2-Methyl-thiazolo[4,5-c]quinoline-hydrochloride $ED_{50}$ = 30 mg/kg i.v.
21 mg/kg s.c.
120 mg/kg p.o.

2-Methyl-thiazolo[4,5-c]quinoline-ethansulfonate $ED_{50}$ = 22 mg/kg s.c.
80 mg/kg p.o.

3. Algolytic test

The experiments were performed according to a method described in detail earlier (Knoll 1967). The essence of the method is that the i.v. or s.c. adminisitration of 10 mg/kg morphine produces complete analgesia in the rat so that laparatomy can be performed without the slightest sign of pain or straining or the appearance of postoperative prostration. Sensation of pain is expressed in arbitrary units on the basis of well defined criteria. Allotting 100 scores for pain reaction in untreated animals and 0 for complete analgesia, the $ED_{100}$ of a drug is the dose which blocks pain completely in the animal and $ED_{50}$ is the dose which reduces the number of scores to 50. Only narcotic analgesics are effective in this test. The test compounds do not influence the surgical pain sensation in the rat.

4. Writhing Test

The method originally described by van der Wende (1956) for rats modified by Witkin et al. (1961) and Koster and Anderson (1959), respectively, for mice was applied. Each dose was administered to a group of ten mice and after 20 min. 60 mg/kg of 0.6% acetc acid solution was injected i.p. As a result of chemical irritation of the peritoneum a characteristic writhing can be observed in 90% of control animals. Ten animals treated with compounds under test were kept under observation for 20 min. following i.p. injection of acid. The analgetic effect of individual doses was expressed in percent:

$$\% \text{ analgetic affect} = 100 - \frac{\text{writhing treated}}{\text{writhing controls}} \times 100$$

The denominator was taken as 90% on the basis of preliminary control examination and the relavant literature.

If we compare the results observed in the hot plate tests, a weaker effectivity in the latter test could be seen. We can conclude therefore that in the hot plate test—which is non selective for the analgesic effect—not only the analgesic, but other, non specific central effects leading also to the prolongation of the reaction time have also been measured.

2-Methyl-thiazolo[4,5-c]quinoline-hydrochloride $ED_{50}$ = 120 mg/kg s.c.

2-Methyl-thiazolo[4,5-c]quinoline-ethanesulphonate $ED_{50}$ = 48 mg/kg s.c.
        145 mg/kg p.o.

5. Narcosis Potentiating Effect

Sleeping times were determined on groups of ten male CFY rats weighing 150–200 g/s. Inactin(35 mg/kg) was injected into the tail vein. The times at which animals lost and regained their righting reflex were recorded. Control sleeping time: 425.59±34.2s (n=120).

Both of the test substances significantly prolong the control barbiturate narcosis time:

2-methyl-thiazolo[4,5-c]quinoline-hydrochloride $ED_{50}$ = 100 mg/kg s.c.
        400 mg/kg p.o.

2-methyl-thiazolo[4,5-c]quinoline-ethanesulphonate $ED_{50}$ = 50 mg/kg s.c.
        170 mg/kg p.o.

6. Modified Jumping Test

This test was elaborated for screening psychoactive drugs. Setup consists of a metal plate of 45° C. and of a glass cylinder with open top and bottom. Animals placed under the glass cylinder on the plate are allowed to jump up once. Latency time between placing and jumping is registered. The time needed for escape (jumping) is taken as an index of central nervous system (CNS) excitability and is expressed in units from 0 to 10. Both salt-forms of the tested compound proved to be ineffective on modified jumping test.

7. Screening Test

Was elaborated for studying learning and retention of rats during one session conditioning.

During conditioning rats are trained to jump onto the top of glass cylinder by the electric foot-shock (110 V). The escape reaction (unconditioned reflex, UR) is paired with a bell as conditioned stimulus. The criterion of learning is that conditioned reflex (CR) should be elicited 10 times with 10 s intervals without reinforcement. Retention of CR is taken positive when 24 h following the experiment CR can be elicited. In these experiments animals are distributed into 4 categories on the basis of their learning ability. Learning is absent when within 20 consecutive trials unconditioned reflex (UR) does not appear; slight, when UR appears, but conditioned reflex (CR) does not; medium when CR-appears following some additional pairings and excellent when CR can be elicited 10 times immediately after pairing.

Both compounds inhibit the development of conditioned reflex in this test. In a dose of 25 mg/kg they cause complete inhibition while 10 mg/kg causes strong inhibition.

A small dose of haloperidol (0.025 mg/kg) resulted in strong inhibition in developing conditioned reflex, while chlordiazepoxide in the same dose does not influence the development of CR.

8. Shuttle-Box

The acquisition of a two-way conditioned avoidance reflex (CAR) was analyzed in the shuttle-box during 5 consecutive days. The instrument was constructed by the Research Institute for Electrical Industry (Hungary). It consists of six boxes, each is separated inside by a barrier with a small gate in the middle. Animals were trained to cross the barrier under the duration of a conditioned stimulus (flash/light) and if they failed to do so they were punished with a footshock (1.3 mA, US). They were given 100 trials per day. One trial consisted of 15 s intertrial interval, followed by 15 s CS. The last 5 s of CS overlapped the first s of US. At each learning session the number of CAR and intersignal reactions (IR) was automatically counted and evaluated by multiway analysis of variance (ANOVA). The two compounds both in doses of 10 and 25 mg/kg strongly inhibited the acquisition of conditioned reflex in the shuttle box. The number of positive responses (F) seemed to be significantly smaller comparing to controls calculated from the first experimental day.

The number of negative responses (−f) in case of 25 mg/kg was high, moreover it was still fairly high when animals were treated 5 mg/kg daily.

The number of intersignal reactions (IR) showed slight fall. 10 and 5 mg/kg chlordiazepoxide left the acquisition of conditioned reflex and IR unchanged, however, in a dose of 10 mg/kg it increased the number of negative responses (f).

9. Measurement of Motility in the Shuttle-Box

The apparatus described in the shuttle-box test is used also for investigating the motility of animals. In case of motility experiment all the stimuli are switched off and the animals are allowed to move freely from one compartment of the box to the other. The number of the spontaneous crossings of the gate during a 30-minute observation period is averaged. Significancy is calculated by Student's test for two means.

The A and B compounds have similar slight motility decreasing effect in this test.

TABLE I

The effect of 2-methyl-thiazolo[4,5-c]quinoline-hydrochloride (A compound) and 2-methyl-thiazolo[4,5-c]quinoline-ethanesulfonate (B compound) on the acquisition of conditioned reflex in a shuttle box. Treatment: s.c. Reference compound: chlordiazepoxide

| Tested compounds | Dose mg/kg | 1 | 2 | 3 | 4 | 5 days |
|---|---|---|---|---|---|---|
| Saline | — | 25.3 | 44.8 | 54.4 | 52.9 | 55.6 |
| A compound | 25 | 7.0$^x$ | 6.6$^x$ | 2.6$^x$ | 1.6$^x$ | 3.1$^x$ |
|  | 10 | 12.0 | 14.7$^x$ | 7.2$^x$ | 5.5$^x$ | 7.3$^x$ |
|  | 5 | 17.8 | 29.6 | 24.3$^x$ | 23.0$^x$ | 29.4$^x$ |
| B compound | 25 | 8.7$^x$ | 4.2$^x$ | 8.9$^x$ | 4.0$^x$ | 2.5$^x$ |
|  | 10 | 7.5$^x$ | 20.2$^x$ | 20.2$^x$ | 17.8$^x$ | 14.5$^x$ |
| Chlordiazepoxide | 25$^x$ | 9.7 | 12.2 | 17.9 | 20.0 | 21.4 |
|  | 10 | 19.9 | 37.9 | 33.7 | 35.6 | 41.2 |
|  | 5 | 23.1 | 38.7 | 35.6 | 41.1 | 50.8 |
| −f |  |  |  |  |  |  |
| Saline | — | 10.3 | 7.1 | 6.1 | 10.3 | 8.0 |
| A compound | 25 | 83.6$^x$ | 85.1$^x$ | 94.3$^x$ | 93.8$^x$ | 95.0$^x$ |
|  | 10 | 70.4$^x$ | 55.3$^x$ | 58.2$^x$ | 66.8$^x$ | 68.2$^x$ |
|  | 5 | 14.4 | 23.0$^x$ | 24.6$^x$ | 25.4 | 27.5 |
| B compound | 25 | 54.9$^x$ | 67.4$^x$ | 74.1$^x$ | 80.1$^x$ | 85.0$^x$ |
|  | 10 | 76.0$^x$ | 40.8$^x$ | 29.3$^x$ | 29.9$^x$ | 37.5$^x$ |
| Chlordiazepoxide | 10 | 32.7$^x$ | 22.8$^x$ | 31.8$^x$ | 36.5$^x$ | 40.8$^x$ |
|  | 25$^x$ | 74.0 | 67.5 | 67.0 | 65.6 | 59.8 |
|  | 5 | 11.8 | 9.1 | 10.2 | 14.9 | 13.0 |
| IR |  |  |  |  |  |  |
| Saline | — | 12.2 | 15.8 | 10.3 | 9.1 | 6.4 |
| A compound | 25 | 10.7 | 5.7 | 4.4$^x$ | 3.8$^x$ | 4.2 |
|  | 10 | 8.9 | 7.3 | 2.7$^x$ | 2.1$^x$ | 2.1 |
|  | 5 | 9.5 | 8.9 | 3.2$^x$ | 2.9$^x$ | 2.3 |
| B compound | 25 | 12.4 | 5.0$^x$ | 9.2 | 4.9$^x$ | 3.3 |
|  | 10 | 11.4 | 9.1 | 7.6 | 4.5$^x$ | 3.3 |
|  | 10 | 10.8 | 14.7 | 8.1 | 6.3 | 6.1 |
| Chlordiazepoxide | 5 | 108 | 14.0 | 8.9 | 6.7 | 4.2 |

Significant. Calculated with Student's t test for 2 means.

10. Effect on Basal Metabolism

The O$_2$ consumption of rats was measured by the method of Issekutz and Issekutz (1952) at constant temperature (30° C.). To inhibit the enhancement of O$_2$ metabolism by possibly increased spontaneous motility, the animals were injected ip.0.6 g/kg urethane. Concentrations as low as this dose do not influence metabolism.

O$_2$ consumption of the animals was expressed in ml/h and calculated for body surface, and given finally in ml/h/dm$^2$. Following injection of urethane and the basal O$_2$ consumption was measured during 30 minutes. This was followed by the injection of the test substance and O$_2$ consumption was registered immediately afterwards. The difference between the highest O$_2$ consumption and the basal value was expressed in percent.

O$_2$ consumption of the animals was calculated according to the following equation:

$$O_2 \text{ consumption} = V \frac{P}{760} \frac{273}{273 + t} \frac{1}{T}, \text{ where}$$

$V = 2000$ cm$^3$
$P =$ pressure fall (mmHg)
$t =$ temperature (30° C.)
$T =$ period of measurement (h)

O$_2$ consumption was calculated for body surface and expressed as ml/dm$^2$/h. Body surface was calculated on the basis of the "Diack" formula:
$s = 7.47^3$ w$^2$ where
$s =$ body surface (cm$^2$)
$w =$ body-weight (g)

2-Methyl-thiazolo[4,5-c]quinoline-hydrochloride slightly, while 2-methyl-thiazolo[4,5-c]quinoline-ethansulphonate strongly and permanently increase the rate of metabolism. The reference compound Haloperidol slightly decreased, while amphetamine dose-dependently increased the O$_2$ consumption.

11. The turnover rate of dopamine (TR$_{DA}$), noradrenaline (TR$_{NA}$) and serotonin (TR$_{5HT}$) was measured 1 hr after the injection of 30 mg/kg s.c. 2-methyl-thiazolo[4,5-c]quinoline-ethanesulphonate.

In brainstem where the serotonergic cell bodies are located the content of 5HT was significantly elevated but the turnover rate was not changed, indicating that the serotonergic neurotransmission remains the same as that of the controls. However, in the teldiencephalon which contains serotonergic nerve terminals the 5HT level was not altered while the TR$_{5\ HT}$ was reduced which was due to the attenuation of the fractional rate constant ($k_b$). The reduced fractional rate constant probably reflects the decreased utilization rate of 5HT.

TABLE II

Changes of 5HT level and turnover rate of 5HT in rat brain parts

| | 5HT ng/g | TR$_{5HT}$ ng/g/hr | K$_b$ hr$^{-1}$ | Brain |
|---|---|---|---|---|
| Control | 395.8 ± 26.5 | 207.9 | 0.81 | Teldiencephalon |
| 2-Methyl-thiazolo-[4,5-c]quinoline-ethanesulphate | 457.9 ± 24.2 | 53.9 | 0.26 | |
| Control | 544.0 ± 71.6 | 255.9 | 0.58 | Brainstem |
| 2-Methyl-thiazolo-[4,5-c]quinoline-ethanesulphate | 792.5 ± 36.9* | 237.2 | 0.50 | |

*p < 0.05

12.

The dopamine content in the striatum was elevated and the fractional rate constant of DA was reduced by the drug. As the changes of the two values compensated each other, the TR$_{DA}$ remained unaltered.

TABLE III

Changes of DA level and turnover rate of DA in rat striatum

| | DA ng/g | TR$_{DA}$ ng/g/hr | k$_b$ hr$^{-1}$ |
|---|---|---|---|
| Control | 6.70 ± 0.45 | 1.5 | 0.23 |
| 2-Methyl-thiazolo | 9.14 ± 0.49* | 1.4 | 0.15 |

TABLE III-continued

| Changes of DA level and turnover rate of DA in rat striatum | | | |
|---|---|---|---|
| | DA ng/g | TR$_{DA}$ ng/g/hr | k$_b$ hr$^{-1}$ |
| [4,5-c]quinoline-ethanesulphonate | | | |

*$p < 0.05$

The high affinity uptake of NA and 5HT was not changed in rat brain cortical P$_2$ fraction 30 and 60 minutes after the injection.

13.

For the studies of benzodiazepine /BZD) receptor binding crude cortical membrane preparation was used. 2 μM $^3$H-diazepam was incubated with the membrane for 1 hr at 0° C. in TRIS-citrate buffer, pH 6.8. Specific binding was determined in the presence of 10 μM diazepam. In displacement studies chlordiazepoxide was used as control drug. Chlordiazepoxide displaced $^3$H-diazepam on the receptor in concentration dependent manner, while the test drug (Formula I) even in high concentration did not alter the specific binding of $^3$H-diazepam.

The 2-methyl-thiazolo[4,5-c]quinoline of the Formula I and pharmaceutically acceptable acid addition salts thereof can be prepared by (a) reacting 3-amino-4-mercapto-quinoline of the Formula II

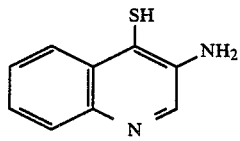

or an acid addition salt thereof with acetic acid of the Formula III

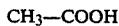 (III)

or a reactive derivative thereof; or (b) reacting 3-amino-quinoline of the Formula II or an acid addition salt thereof with acetaldehyde of the Formula V

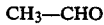 (V)

in the presence of air; or (c) cyclising 3-acetamido-4-mercapto-quinoline of the formula IV

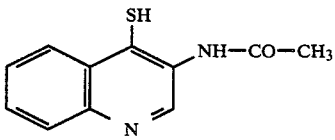

and, if desired, converting the 2-methyl-thiazolo[4,5-c]quinoline of the Formula I into a pharmaceutically acceptable acid addition salt thereof or transforming the compound of the Formula I or an acid addition salt thereof into a hydrate or setting free the compound of the Formula I from a salt thereof.

According to process (a) 3-amino-4-mercapto-quinoline of the Formula II or an acid addition salt thereof is reacted with acetic acid or a reactive derivative thereof. As reactive derivative of acetic acid preferably acetic anhydride, a triethyl ortho acetate, an acetyl halide or an ester or acetic acid may be used. One may proceed particularly advantageously by using a trialkyl ortho acetate. The reactive derivative of acetic acid (e.g. acetic anhydride or triethyl ortho acetate) may be used in an excess, when it serves as reaction medium, too. One may also proceed by using the compound of the Formula II and acetic acid or a reactive derivative thereof in equimolar amounts and carrying out the reaction in the presence of an inert solvent. As reaction medium preferably aromatic hydrocarbons (e.g. benzene, toluene or xylene) can be used. The reaction may be accomplished at a temperature between 20° C. and 160° C., one may preferably work at the boiling point of the reaction mixture.

According to a particularly preferred embodiment of process (a) 3-amino-4-mercapto-quinoline of the Formula II is reacted with an excess of a trialkyl ortho acetate at a temperature between 100° C. and 160° C., preferably at a temperature being by 5°–10° C. lower than the boiling point of the trialkyl ortho acetate, and removing from the reaction mixture continuously the alkanol formed in the reaction. One may preferably use triethyl ortho acetate. The reaction having been completed, the reaction mixture is cooled to room temperature.

The compound of the Formula I can be isolated from the reaction mixture in the form of the free base or an acid addition salt thereof by known method (e.g. extraction, cooling, evaporation or filtration).

According to process (b) 3-amino-4-mercapto-quinoline of the Formula II or an acid addition salt thereof (preferably the hydrochloride) is reacted with acetaldehyde of the Formula V in the presence of air. The reaction may be preferably accomplished in the presence of an inert organic solvent. As reaction medium advantageously an alkanol (e.g. methanol, ethanol or isopropanol) can be used. The reaction may be carried out at 20°–160° C., preferably at the boiling point of the reaction mixture. The acetaldehyde may be used in equimolar amount or in a slight excess (5–20%).

The compound of the Formula I can be isolalted from the reaction mixture by known methods (e.g. cooling, dilution with water, filtration).

According to process (c) 3-acetamido-4-mercapto-quinoline of the Formula IV is subjected to cyclization. Ring closure may be preferably carried out in an inert solvent. As reaction medium preferably an aromatic hydrocarbon (e.g. benzene, toluene or xylene) or a halogenated hydrocarbon (e.g. chlorobenzene) can be used. The reaction may be carried out at elevated temperature, particularly at 100°–180° C.

Cyclization may be enhanced by carrying out the reaction in the presence of a dehydrating agent. Polyphosphoric acid proved to be particularly useful for this purpose. One may particularly advantageously proceed by carrying out the reaction in an excess of polyphosphoric acid as reaction medium under heating in the absence of an organic solvent.

The compound of the Formula I can be isolated from the reaction mixture by known methods (e.g. dilution with water, alkalization, extraction with an organic solvent).

The compound of the Formula I may be converted into a pharmaceutically acceptable acid addition salt by reacting with the corresponding acid. Salt formation may be accomplished in a manner known per se. The base of the Formula I can be set free from the acid addition salts by methods known per se.

The starting materials of the Formulae II and IV are known and can be prepared as described in prior art [J. Am. Chem. Soc. 69, 365–371 (1947)].

The other starting materials (acetic acid, reactive derivatives thereof and acetaldehyde) are industrial scale commercial products.

The pharmaceutical compositions according to the present invention comprise the 2-methyl-thiazolo[4,5-c]quinoline of the Formula I or a pharmaceutically acceptable acid addition salt or hydrate of the base of the Formula I or an acid addition salt thereof in admixture with suitable inert solid or liquid pharmaceutical carriers. The pharmaceutical compositions can be suitable for oral (e.g. tablets, coated pills, dragees, hard or soft gelatin capsules, solutions, emulsions or suspensions), parenteral (e.g. injectable solutions) or rectal (e.g. suppositories) administration.

The pharmaceutical compositions of the present invention can be prepared by known methods of pharmaceutical industry by admixing the 2-methyl-thiazolo[4,5-c]quinoline of the Formula I or a pharmaceutically acceptable acid addition salt or hydrate thereof with suitable inert solid or liquid pharmaceutical carriers and finishing the mixture in galenic form.

Tablets, coated pills, dragees and hard gelatine capsules may comprise as carrier e.g. lactose, maize starch, talc, magnesium carbonate, magnesium stearate, calcium carbonate, stearic acid or salts thereof etc. Soft gelatin capsules may comprise as carrier e.g. vegetable oils, fats, wax or polyols of suitable consistence. When preparing solutions or syrups, e.g. water, polyols, polyethylene glycol, saccharose or glucose may be used as carrier. Injectable solutions may comprise e.g. water, alcohols, polyols, glycerol or vegetable oils as carrier. Suppositories may comprise as carrier e.g. oils, wax, fats, cocoa butter or polyols of suitable consistence.

The pharmaceutical compositions of the present invention may also comprise conventional auxiliary agents generally used in pharmaceutical industry. From the broad scope of conventional additives the wetting, dispersing, conserving, emulsifying agents, solubilizers, colouring agents, sweetening agents, aroma substances and salts suitable for modifying the osmotic pressure can be mentioned.

The daily dosage of the 2-methyl-thiazolo[4,5-c]quinoline may vary between wide ranges. Just of informative character it can be noticed that the dose of the compound of the Formula I on oral administration may be between about 20 mg/kg and about 1000 mg/kg, while the parenteral dose may amount to from about 5 mg/kg to about 250 mg/kg. We wish to note that the above intervals are but of an approximate nature and the actual dose always depends on various factors (e.g. seriousness of the disease, age and condition of the patient etc.) and is determined by the physician. The actual dose may be below or above the said limits, too.

Further details of the present invention are to be found in the following Examples without limiting the scope of protection to the said Examples.

EXAMPLE 1

A mixture of 17.62 g (0.1 mole) of 3-amino-4-mercapto-quinoline and 70 ml of acetic anhydride is heated slowly to the boiling point and thereafter heated to boiling for one hour and a half. The reaction mixture is cooled and 600 ml of 1% hydrochloric acid are added dropwise under vigorous stirring. The homogenous solution is made alkaline with a sodium hydroxide solution and the precipitated base is extracted three times with 100 ml of benzene each. The united benzene extracts are clarified, dried and evaporated in vacuo. Thus 2-methyl-thiazolo[4,5-c]quinoline is obtained, m.p.: 99°–100° C. (after recrystallization from a mixture of methanol and water).

EXAMPLE 2

A mixture of 17.62 g (0.1 mole) of 3-amino-4-mercapto-quinoline, 180 ml of acetic acid and 1.5 g of sodium pyrosulfite is refluxed for 4 hours. The reaction mixture is worked up as described in Example 1. The melting point of the 2-methyl-thiazolo[4,5-c]quinoline amounts to 99°–100° C.

EXAMPLE 3

A mixture of 10.9 g (0.05 mole) of 3-acetamido-4-mercapto-quinoline and 100 g of polyphosphoric acid is heated at 140°–160° C. for 2 hours, then cooled to 90° C., whereupon 600 ml of water are added under further cooling and constant stirring. When the reaction mixture is cooled to 20° C., it is made alkaline by adding a 40% sodium hydroxide solution, the mixture comprising a precipitate is extracted three times with 200 ml of benzene each. The benzene solution is evaporated. The 2-methyl-thiazolo[4,5-c]quinoline thus obtained melts at 99°–100° C.

EXAMPLE 4

21.27 g (0.1 mole) of 3-amino-4-mercapto-quinoline hydrochloride are admixed with 200 ml of triethyl ortho acetate and the reaction mixture is heated slowly to 120°–140° C. while the ethanol formed is continuously distilled off. The reaction mixture is heated at this temperature for 30 minutes, then cooled and ethanol comprising hydrochloric acid and 100 ml of ethyl acetate are added successively in order to make crystallization complete. The 2-methyl-thiazolo[4,5-c]quinoline-hydrochloride thus obtained melts at 249°–245° C., (the m.p disclosed in prior art amounts to 240°–245° C., decomposition).

EXAMPLE 5

20.0 g (0.1 mole) of 2-methyl-thiazolo[4,5-c]quinoline are dissolved in 150 ml of benzene, whereupon 11 g (0.1 mole) of ethane sulfonic acid are added dropwise under cooling. The reaction mixture is stirred for a short time, the precipitated crystals are filtered, washed and dried. The melting point of the 2-methyl-thiazolo[4,5-c]quinoline-ethanesulfonate-hydrate thus obtained is 144°–146° C.

Analysis: Calc.: C %=47.54; N %=8.53; S %=19.52; Found: C%=47.83; N %=8.42; S %=19.41.

EXAMPLE 6

Tablets having the following composition are prepared:

| Component | Amount, mg/tablet |
|---|---|
| 2-Methyl-thiazolo[4,5-c]quinoline-ethanesulfonate | 25.0 |
| Maize starch | 97.0 |

| Component | Amount, mg/tablet |
|---|---|
| Polyvinyl pyrrolidone | 175.0 |
| Magnesium stearate | 3.0 |
| Total weight | 300.0 |

The mixture of the active ingredient and maize starch is moistened with a 10–15% polyvinyl pyrrolidone solution, granulated and dried. The granules are thoroughly dried, admixed with the magnesium stearate and pressed to tablets.

EXAMPLE 7

Capsules having the following composition are prepared by methods of pharmaceutical industry known per se:

| Component | Amount, mg/capsule |
|---|---|
| 2-Methyl-thiazolo[4,5-c]quinoline-hydrochloride | 20.0 |
| Lactose | 60.0 |
| Maize starch | 17.0 |
| Talc | 2.0 |
| Magnesium stearate | 1.0 |
| Total weight | 100.0 |

What we claim is:

1. Ethanesulfonate salt of 2-methyl-thiazolo[4,5-c]-quinoline, or a hydrate thereof.

2. A method of depressing the central nervous system of a warm blooded animal patient which comprises administering to said patient an effective amount of 2-methyl-thiazole[4,5-c]-quinoline or a pharmaceutically acceptable acid addition salt thereof or a hydrate thereof or an acid addition salt of the hydrate, whereby a CNS depressing effect is produced in said patient.

3. A pharmaceutical composition for depressing the central nervous system of a warm blooded animal patient comprising a therapeutically effective amount of the ethane sulfonate salt of 2-methyl-thiazolo [4,5-c]-quinoline, in admixture with an inert solid or liquid pharmaceutically acceptable carrier.

4. The method of claim 2, wherein the active agent is the ethane sulfonate salt of 2-methyl-thiazolo[4,5-c]-quinoline or a hydrate thereof.

5. The method of claim 2, wherein the active agent is 2-methyl-thiazolo[4,5-c]-quinoline-hydrochloride or a hydrate thereof.

* * * * *